US010980857B2

(12) United States Patent
Barrandon et al.

(10) Patent No.: US 10,980,857 B2
(45) Date of Patent: Apr. 20, 2021

(54) TREATMENT WITH GDF11 PREVENTS WEIGHT GAIN, IMPROVES GLUCOSE TOLERANCE AND REDUCES HEPATOSTEATOSIS

(71) Applicants: President and Fellows of Harvard College, Cambridge, MA (US); The Brigham and Women's Hospital, Inc., Boston, MA (US)

(72) Inventors: Ornella Barrandon, Cambridge, MA (US); Tommaso Poggioli, Boston, MA (US); Douglas A. Melton, Lexington, MA (US); Richard T. Lee, Weston, MA (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/068,463

(22) PCT Filed: Jan. 6, 2017

(86) PCT No.: PCT/US2017/012505
§ 371 (c)(1),
(2) Date: Jul. 6, 2018

(87) PCT Pub. No.: WO2017/120450
PCT Pub. Date: Jul. 13, 2017

(65) Prior Publication Data
US 2019/0015479 A1 Jan. 17, 2019

Related U.S. Application Data

(60) Provisional application No. 62/275,645, filed on Jan. 6, 2016.

(51) Int. Cl.
*A61K 38/18* (2006.01)
*C07K 14/00* (2006.01)
*A61P 3/04* (2006.01)
*A61P 3/06* (2006.01)
*A61P 3/10* (2006.01)
*A61K 38/19* (2006.01)
*C07K 14/475* (2006.01)
*C12N 5/00* (2006.01)

(52) U.S. Cl.
CPC .......... *A61K 38/1841* (2013.01); *A61K 38/18* (2013.01); *A61K 38/19* (2013.01); *A61P 3/04* (2018.01); *A61P 3/06* (2018.01); *A61P 3/10* (2018.01); *C07K 14/00* (2013.01); *C07K 14/475* (2013.01); *C12N 5/00* (2013.01)

(58) Field of Classification Search
CPC .......................... A61K 38/1841; A61K 38/19
See application file for complete search history.

(56) References Cited

U.S. PATENT DOCUMENTS

| | | |
|---|---|---|
| 5,639,638 A | 6/1997 | Wozney et al. |
| 5,700,911 A | 12/1997 | Wozney et al. |
| 6,008,434 A | 2/1999 | Lee et al. |
| 6,340,668 B1 | 1/2002 | Celeste et al. |
| 6,517,835 B2 | 2/2003 | Lee et al. |
| 6,555,672 B1 | 4/2003 | Liang |
| 6,656,475 B1 | 12/2003 | Lee et al. |
| 6,696,260 B1 | 2/2004 | Lee et al. |
| 7,175,997 B2 | 2/2007 | Wozney et al. |
| 7,202,210 B2 | 4/2007 | Wolfman et al. |
| 7,384,753 B2 | 6/2008 | Lee et al. |
| 7,560,441 B2 | 7/2009 | Wolfman et al. |
| 7,572,440 B2 | 8/2009 | Vukicevic et al. |
| 7,709,605 B2 | 5/2010 | Knopf et al. |
| 7,976,839 B2 | 7/2011 | Lee et al. |
| 8,067,562 B2 | 11/2011 | Han et al. |
| 8,168,169 B2 | 5/2012 | Cataldo et al. |
| 8,222,384 B2 | 7/2012 | Wolfman et al. |
| 8,323,964 B2 | 12/2012 | Lee et al. |
| 8,952,130 B2 | 2/2015 | Choe et al. |
| 9,434,779 B2 | 9/2016 | Lee et al. |
| 10,017,566 B2 | 7/2018 | Lee |

(Continued)

FOREIGN PATENT DOCUMENTS

| | | |
|---|---|---|
| EP | 1378572 | 10/2006 |
| EP | 2309261 | 4/2011 |

(Continued)

OTHER PUBLICATIONS

Alaoui-Ismaili, et al.,"Design of Second Generation Therapeutic Recombinant Bone Morphogenetic Proteins," *Cytokine Growth Factor Rev.*, 20:501-507, (2009).
Breitbart, "Myostatin from the Heart: Local and Systemic Actions in Cardian Failure and Muscle Wasting," *Am. J. Physiol. Heart Circ. Physiol.*, 300(6):H1973-H1982, (2011).
Conboy, et al., "Heterochronic Parabiosis for the Study of the Effects of Aging on Stem Cells and Their Niches," *Cell Cycle*, 11(12):2260-2267, (2012).

(Continued)

*Primary Examiner* — Gyan Chandra
(74) *Attorney, Agent, or Firm* — Morse, Barnes-Brown & Pendleton, P.C.; Lisa M. Warren, Esq.

(57) ABSTRACT

Disclosed herein are a means to prevent and/or ameliorate age, disease and obesity associated metabolic diseases, such as diabetes and impaired glucose tolerance. Also disclosed are compositions and methods that relate to the findings that GDF11 prevents weight gain, improves glucose tolerance and reduces hepatosteatosis in aged mice administered a high fat diet. In particular, the methods and compositions described herein relate to increasing the level of GDF11 in a subject, thereby treating or preventing the development of obesity in the subject, reducing the metabolic consequences of obesity and improving the subject's metabolic health.

13 Claims, 8 Drawing Sheets
Specification includes a Sequence Listing.

(56) References Cited

U.S. PATENT DOCUMENTS

| | | |
|---|---|---|
| 2002/0150577 A1 | 10/2002 | Lee et al. |
| 2003/0083252 A1 | 5/2003 | Celeste et al. |
| 2003/0104977 A1 | 6/2003 | Ripamonti et al. |
| 2003/0167492 A1 | 9/2003 | Lee et al. |
| 2003/0170213 A1 | 9/2003 | Charette |
| 2003/0224501 A1 | 12/2003 | Young et al. |
| 2005/0197367 A1 | 9/2005 | Li et al. |
| 2006/0078532 A1 | 4/2006 | Omoigui |
| 2006/0172391 A1 | 8/2006 | Wozney et al. |
| 2006/0216279 A1 | 9/2006 | Glass et al. |
| 2007/0253962 A1 | 11/2007 | Hirsch et al. |
| 2007/0275895 A1 | 11/2007 | Duan et al. |
| 2008/0044387 A1 | 2/2008 | Conboy et al. |
| 2008/0051328 A1 | 2/2008 | Sharma et al. |
| 2009/0215671 A1 | 8/2009 | Calof et al. |
| 2009/0263402 A1 | 10/2009 | Lee et al. |
| 2009/0298761 A1 | 12/2009 | Engelman |
| 2010/0196332 A1 | 8/2010 | Wichterle et al. |
| 2010/0221777 A1 | 9/2010 | Choe et al. |
| 2011/0027177 A1 | 2/2011 | Jacoby et al. |
| 2011/0105395 A1 | 5/2011 | Fallon et al. |
| 2011/0200580 A1 | 8/2011 | Karp et al. |
| 2013/0071393 A1 | 3/2013 | Seehra et al. |
| 2013/0108645 A1 | 5/2013 | Farah |
| 2013/0156767 A1 | 6/2013 | Walsh et al. |
| 2015/0045297 A1 | 2/2015 | Lee et al. |
| 2015/0218522 A1 | 8/2015 | Peterson et al. |
| 2015/0239950 A1 | 8/2015 | Choe et al. |
| 2016/0074477 A1 | 3/2016 | Wagers et al. |
| 2016/0220640 A1 | 8/2016 | Rubin et al. |
| 2016/0264657 A1 | 9/2016 | Lee et al. |
| 2016/0287667 A1 | 10/2016 | Wagers |
| 2017/0298128 A1 | 10/2017 | Barnes et al. |
| 2018/0340022 A1 | 11/2018 | Lee |

FOREIGN PATENT DOCUMENTS

| | | |
|---|---|---|
| EP | 1790726 | 7/2013 |
| WO | WO 1994/26892 | 11/1994 |
| WO | WO 98/35019 | 8/1998 |
| WO | WO 99/024057 | 5/1999 |
| WO | WO 99/24058 | 5/1999 |
| WO | WO 1999/037320 | 7/1999 |
| WO | WO 2002/010214 | 2/2002 |
| WO | WO 2002/068650 | 9/2002 |
| WO | WO 2004/073633 | 9/2004 |
| WO | WO 2005/094446 | 10/2005 |
| WO | WO 2006/116269 | 11/2006 |
| WO | WO 2008/109167 | 9/2008 |
| WO | WO 2010/099219 | 9/2010 |
| WO | WO 2012/135623 | 10/2012 |
| WO | WO 2013/142114 | 9/2013 |
| WO | WO 2014/168973 | 10/2014 |
| WO | WO 2014/201143 | 12/2014 |
| WO | WO 2015/034897 | 3/2015 |
| WO | WO 2015/070076 | 5/2015 |
| WO | WO 2015/073396 | 5/2015 |
| WO | WO 2015/171691 | 11/2015 |
| WO | WO 2016/049662 | 3/2016 |
| WO | WO 2017/120450 | 7/2017 |
| WO | WO-2018/067754 A1 | 4/2018 |

OTHER PUBLICATIONS

Dai, et al., "Overexpression of Catalase Targeted to Mitochondria Attenuates Murine Cardiac Aging," *Circulation* 119(21):2789-2797, (2009).

Gamer, et al., "GDF11 is a Negative Regulator of Chondrogenesis and Myogenesis in the Developing Chick Limb," *Developmental Biology*, 229(2):407-420, (2001).

Gano, et al.,"Ketogenic Diets, Mitochondria, and Neurological Diseases," *J. Lipid Res.*, 55:2211-2228, (2014).

Geng, et al.,"Molecular Cloning and Expression Analysis of Porcine Bone Morphogenetic Protein 11 (BMP11) Gene," *Journal of Animal and Veterinary Advances*, 9(23):2986-2989, (2010).

Gleeson, et al., "Neuromuscular Diseases in Geriatric Patients: Part I," *Consultant360*, 18(2):1-12, (Feb. 2010).

Guo, et al.,"Protein Tolerance to Random Amino Acid Change," *PNAS*, 101(25):9205-9210, (Jun. 22, 2004).

Harmon, et al., "GDF11 Modulates NGN3+ Islet Progenitor Cell Number and Promotes Beta Cell Differentiation in Pancreas Development," *Development*, 131(24):6163-6174, (2004).

Japanese Patent Application Kohyo Publication No. H09-501304 (unexamined Japanese national phase publication corresponding to a non-Japanese International publication)(JPH09501304A).

Krivickas, et al., "Exercise in Neuromuscular Disease," *J. Clin. Neuro, Disease*, 5(1):29-39, (Sep. 2003).

Li, et al.,"Changes in Aging Mouse Neuromuscular Junctions are Explained by Degeneration and Regeneration of Muscle Fiber Segments at the Synapse," *J. Neurosci.*, 31(42):14910-14919, (Oct. 19, 2011).

Li, et al.,"Transgenic OverExpression of Bone Morphogenetic Protein 11 Propeptide in Skeleton Enhances Bone Formation," *Biochemical and Biophysical Research Communications*, 416(3):289-292, (2011).

Lima, et al.,"Myostatin and Follistatin Expression in Skeletal Muscles of Rats with Chronic Heart Failure," *Int. J. Exp. Path.*, 91(1):54-62, (2010).

McPherron, et al., "Redundancy of Myostatin and Growth/Differentiation Factor 11 Function," *BMC Developmental Biology*, 9:1-9, (2009).

Morissette, et al., "Myostatin Regulates Cardiomyocyte Growth Through Modulation of AKT Signaling," *Circ, Res.*, 99(1):15-24, (2006).

Paoli, et al., "Ketogenic Diet in Neuromuscular and Neurodegenerative Diseases," *BioMed Res. Intl.*, (ID474296):1-10, (2014).

Shyu, et al., "Myostatin Expression in Ventricular Myocardium in a Rat Model of Volume-Overload Heart Failure," *European Journal of Clinical Investigation*, 36:713-719, (2006).

Tsuchida, et al., "Activin Signaling as an Emerging Target for Therapeutic Interventions," *Cell Communication and Signaling*, 7(1):1-11, (2009).

Zhou, et al., "Reversal of Cancer Cachexia and Muscle Wasting by ActRIIB Antagonism Leads to Prolonged Survival," *Cell* 142:531-543, (2010).

Final Office Action for U.S. Appl. No. 14/897,605, dated Sep. 30, 2019.

Non-Final Office Action for U.S. Appl. No. 16/442,437, dated Oct. 1, 2019.

Glass, D.J., "Elevated GDF11 Is a Risk Factor for Age-Related Frailty and Disease in Humans," *Cell Metabolism*, 24:7-8, (Jul. 12, 2016).

Jones, et al., "Supraphysiologic Administration of GDF11 Induces Cachexia in Part by Upregulating GDF 15," *Cell Reports*, 22:1522-1530, (Feb. 6, 2018).

Ming, et al., "Adult Neurogenesis in the Mammalian Central Nervous System," *Annu. Rev. Neurosci* 28:223-250, (2005).

Oshima, et al., "Follistatin-Like 1 Is an Akt-Regulated Cardioprotective Factor That Is Secreted by the Heart," *Circulation* 117:3099-3108, (2008).

Rodgers, et al., "Reduced Circulating GDF11 Is Unlikely Responsible for Age-Dependent Changes in Mouse Heart, Muscle, and Brain," *Endocrinology* 156(11):3885-3888 (Nov. 2015).

Schafer, et al., "Quantification of GDF11 and Myostatin in Human Aging and Cardiovascular Disease," *Cell Metabolism* 23:1207-1215, (Jun. 14, 2016).

Shi, et al., "Gdf11 Facilitates Temporal Progression of Neurogenesis in the Developing Spinal Cord," *The Journal of Neuroscience* 31(3):883-893, (Jan. 19, 2011).

Shimano, et al., "Cardiac Myocyte Follistatin-Like 1 Functions to Attenuate Hypertrophy Following Pressure Overload," published online www.pnas.org/cgi/doi/10.1073/pnas.1108559108(2011).

Non-Final Office Action for U.S. Appl. No. 15/035,331, dated Dec. 14, 2018.

Non-Final Office Action for U.S. Appl. No. 14/897,605, dated Dec. 18, 2018.

Final Office Action for U.S. Appl. No. 15/513,979, dated Dec. 13, 2018.

(56) References Cited

OTHER PUBLICATIONS

Andersson, et al., "Growth Differentiation Factor 11 Signals Through the Transforming Growth Factor-β Receptor ALK5 to Regionalize the Anterior-Posterior Axis," *EMBO Reports*, 7(8)831-837, (2006).
Anger, "Animal Test Systems to Study Behavioral Dysfunction," *Neurotoxicology*, 12(3):403-413, (1991).
Aziz, et al. "Diastolic Heart Failure: A Concise Review," *J. Clin. Med. Res*., 5(5):327-334, (2013).
Bowie, et al., "Deciphering the Message in Protein Sequences: Tolerance to Amino Acid Substitutions," *Science*, 247(4948):1306-1310, (Mar. 16, 1990).
Brack, "Ageing of the Heart Reversed by Youthful Systemic Factors," *The EMBO Journal*, 32:2189-2190, (2013).
Brun, et al., "GDF11 and the Mythical Fountain of Youth," *Cell Metabolism*, 22:56-54, (2015).
Burgess, et al., "Possible Dissociation of the Heparin Binding and Mitogenic Activities of Heparin-Binding (Acidic Fibroblast) Growth Factor-1 from Its Receptor-Binding Activities by Site-Directed Mutagenesis of a Single Lysine Residue," *Journal of Cell Biology*, 111:2129-2138, (1990).
Coyle, et al., "Physical Activity as a Metabolic Stressor," *Am. J. Clin. Nutr*., 72:512S-20S, (2000).
Egerman, et al., "GDF11 Increases with Age and Inhibits Skeletal Muscle Regeneration," Cell Metabolism 22: 164-174, (2015).
Hannan, et al., "BMP-11 and Myostatin Support Undifferentiated Growth of Human Embryonic Stem Cells in Feeder-Free Cultures," *Cloning and Stem Cells*, 11(3):427-435, (2009).
Harper, et al., "Is Growth Differentiation Factor 11 a Realistic Therapeutic for Aging-Dependent Muscle Defects," *Cir. Res*., 118(7):1143-1150, (Apr. 1, 2016).
Katsimpardi, et al., "Vascular and Neurogenic Rejuvenation of the Aging Mouse Brain by Young Systemic Factors," *Science*, 344:630-634, (May 9, 2014).
Krakora, et al., "Neuromuscular Junction Protection for the Potential Treatment of Amyotrophic Lateral Sclerosis," Hindawi Publishing Corporation Neurology Research International vol. 2012; 8 pages.
Lach-Trifilieff, et al., "An Antibody Blocking Activin Type II Receptors Induces Strong Skeletal Muscle Hypertrophy and Protects from Atrophy," *Mol. Cell. Biol*. Doi:10.1128/MCB, published online Dec. 2, 2013, pp. 1-40.
Lara-Pezzi, et al., "Abstract 2459: A Potentially Novel Role of the Follistatin-Activin Pathway in Heart Failure and Myocardial Recovery Following Lvad Combination Therapy," *Circulation*, 116:116:II_541, pp. 1-3, (2007).
Lee, et al., "Regulation of GDF-11 and Myostatin Activity by GASP-1 and GASP-2," *Prc Natl Acad Sci USA*, 110(39):3713-3722, (Sep. 2013).
Loffredo, et al., "Heart Failure with Preserved Ejection Fraction: Molecular Pathways of the Aging Myocardium," *Circ Res*, 115(1):97-107, (Jun. 2014).
Loffredo, et al., Growth Differentiation Factor 11 is a Circulating Factor that Reverses Age-Related Cardiac Hypertrophy, *Cell* 153(4):828-839, (May 2013).
Marzetti, et al., "Mitochondrial Death Effectors: Relevance to Sarcopenia and Disuse Muscle Atrophy," *Biochim Biophys Acta*, 1800(3):235-44, (2010).
Nedachi, et al., "Contractile C2C12 Myotube Model for Studying Exercise-Inducible Responses in Skeletal Muscle," *Am J Physiol Endocrinol Metab*., 295(5):E1191-204, (2008).
Pawson, et al., "Assembly of Cell Regulatory Systems Through Protein Interaction Domains," *Science*, 300:445-452, (Apr. 18, 2003).
Ruckh, et al., "Rejuvenation of Regeneration in the Aging Central Nervous System," *Cell Stem Cell*, 10(1):96-103, (2012).
Shimano, et al., "Cardiac Myocyte-Specific Ablation of Follistatin-Like 3 Attenuates Stress-Induced Myocardial Hypertrophy," *Journal of Biological Chemistry*, 286(11):9840-9848, (Mar. 18, 2011).
Souza, et al., "Proteomic Identification and Functional Validation of Activins and Bone Morphogenetic Protein 11 as Candidate Novel Muscle Mass Regulators," *Molecular Endocrinology*, 22(12):2689-2702, (2008).
Tayebati, "Animal Models of Cognitive Dysfunction," *Mechanisms of Ageing and Development*, 127:100-108, (2006).
Wagers, A., "Systemic Regulation of Aging Phenotypes in Mammalian Tissues," HHMI, Harvard University, and Joslin Diabetes Center, Sep. 26, 2013.
Wagers, et al., "Cellular and Molecular Signatures of Muscle Regeneration: Current Concepts and Controversies in Adult Myogenesis," *Cell*, 122:659-667, (2005).
Wu, et al., "Autoregulations of Neurogenesis by GDF-11," *Neuron*, 37:197-207, (Jan. 23, 2003).
Zhu, et al., "Follistatin Improves Skeletal Muscle Healing After Injury and Disease Through an Interaction With Muscle Regeneration, Angiogenesis, and Fibrosis," *Am J Pathol*., 179(2):915-30, (2011).
Extended European Search Report from EP 14782154.0, dated Nov. 8, 2016.
International Search Report from PCT/US2014/041952, dated Oct. 31, 2014.
International Search Report from PCT/US2014/33376, dated Sep. 26, 2015.
International Search Report from PCT/US2014/064648, dated May 20, 2015.
International Search Report from PCT/US2015/062226, dated Mar. 4, 2016.
Extended European Search Report from EP 14810402.9, dated Feb. 13, 2017.
International Search Report for PCT/US2017/012505, dated May 4, 2017.
Non-Final Office Action from U.S. Appl. No. 14/897,605, dated Dec. 14, 2016.
Non-Final Office Action from U.S. Appl. No. 15/035,331 dated Apr. 20, 2017.
Final Office Action for U.S. Appl. No. 14/897,605, dated May 23, 2017.
Final Office Action for U.S. Appl. No. 15/035,331, dated Nov. 2, 2017.
Final Office Action for U.S. Appl. No. 14/897,605, dated Nov. 2, 2017.
Non-Final Office Action for U.S. Appl. No. 14/783,426, dated Dec. 26, 2017.
Non-Final Office Action for U.S. Appl. No. 15/513,979, dated Mar. 29, 2018.
Notice of Allowance for U.S. Appl. No. 14/783,426, dated Jun. 8, 2018.
Casset, et al.,"A Peptide Mimetic of an Anti-CD4 Monoclonal Antibody by Rational Design," *Biochemical and Biophysical Research Communication*, 307:198-205, (2003).
Chen, et al., "Selection and Analysis of an Optimized Anti-VEGF Antibody: Crystal Structure of an Affinity-Matured Fab in Complex with Antigen," *J. Mol. Biol*., 293:865-881, (1999).
DePascalis, et al.,"Grafting of "Abbreviated" Complementarity-Determining Regions Containing Specificity-Determining Residues Essential for Ligand Contact to Engineer a Less Immunogenic Humanized Monoclonal Antibody," *The Journal of Immunology*, 169(6):3076-3084, (Oct. 2002).
Fan, et al., "Cardiac Fibroblasts, Fibrosis and Extracellular Matrix Remodeling in Heart Disease," *Fibrogenesis & Tissue Repair*, 5(15):1-13, (2012).
Holm, et al.,"Functional Mapping and Single Chain Construction of the Anti-Cytokeratin 8 Monoclonal Antibody TS1," *Molecular Immunology* 44:1075-1084, (2007).
MacCallum, et al., "Antibody-Antigen Interactions: Contact Analysis and Binding Site Topography," *J. Mol. Biol*., 262:732-745, (1996).
Moreo, et al., "Influence of Myocardial Fibrosis on Left Ventricular Diastolic Function," Circulation: *Cardiovascular Imaging*, 2(6):437-443, (Nov. 2009).

(56) References Cited

OTHER PUBLICATIONS

Oshima, "Activin A and Follistatin-Like 3 Determine the Susceptibility of Heart to Ischemic Injury," *Circulation*, 120(16):1606-1615, (Oct. 20, 2009).
Panse, et al., "Follistatin-Like 3 Mediates Paracrine Fibroblast Activation by Cardiomyocytes," *J. of Cardiovasc. Trans. Res.*, 5:814-826, (2012).
Rudikoff, et al., "Single Amino Acid Substitution Altering Antigen-Binding Specificity," *Proc. Natl. Acad. Sci. USA*, 79:1979-1983, (Mar. 1982).
Schneyer, et al.,"Diabetes Mellitus and Glucose Metabolism," *JESOCI*, 4, Abstract Supplement, p. A939, (2020).
Vajdos, et al., "Comprehensive Functional Maps of the Antigen-Binding Site of an Anti-ErbB2 Antibody Obtained with Shotgun Scanning Mutagenesis," *J. Mol. Biol*, 320:415-428, (2002).
Wu, et al., "Humanization of a Murine Monoclonal Antibody by Simultaneous Optimization of Framework and CDR Residues," *J. Mol. Biol.*, 294:151-162, (1999).
Non-Final Office Action for U.S. Appl. No. 15/513,979, dated May 19, 2020.
Final OA from U.S. Appl. No. 16/442,437, dated Jul. 10, 2020.
Non-Final Office Action from U.S. Appl. No. 16/154,691, dated Jan. 21, 2021.

SEQ ID NO: 1

```
Met Val Leu Ala Ala Pro Leu Leu Leu Gly Phe Leu Leu Leu Ala Leu
1               5                   10                  15
Glu Leu Arg Pro Arg Gly Glu Ala Ala Glu Gly Pro Ala Ala Ala Ala
            20                  25                  30
Ala Ala Ala Ala Ala Ala Ala Ala Ala Gly Val Gly Gly Glu Arg Ser
        35                  40                  45
Ser Arg Pro Ala Pro Ser Val Ala Pro Glu Pro Asp Gly Cys Pro Val
    50                  55                  60
Cys Val Trp Arg Gln His Ser Arg Glu Leu Arg Leu Glu Ser Ile Lys
65                  70                  75                  80
Ser Gln Ile Leu Ser Lys Leu Arg Leu Lys Glu Ala Pro Asn Ile Ser
                85                  90                  95
Arg Glu Val Val Lys Gln Leu Leu Pro Lys Ala Pro Pro Leu Gln Gln
            100                 105                 110
Ile Leu Asp Leu His Asp Phe Gln Gly Asp Ala Leu Gln Pro Glu Asp
            115                 120                 125
Phe Leu Glu Glu Asp Glu Tyr His Ala Thr Thr Glu Thr Val Ile Ser
    130                 135                 140
Met Ala Gln Glu Thr Asp Pro Ala Val Gln Thr Asp Gly Ser Pro Leu
145                 150                 155                 160
Cys Cys His Phe His Phe Ser Pro Lys Val Met Phe Thr Lys Val Leu
                165                 170                 175
Lys Ala Gln Leu Trp Val Tyr Leu Arg Pro Val Pro Arg Pro Ala Thr
            180                 185                 190
Val Tyr Leu Gln Ile Leu Arg Leu Lys Pro Leu Thr Gly Glu Gly Thr
    195                 200                 205
Ala Gly Gly Gly Gly Gly Arg Arg His Ile Arg Ile Arg Ser Leu
210                 215                 220
Lys Ile Glu Leu His Ser Arg Ser Gly His Trp Gln Ser Ile Asp Phe
225                 230                 235                 240
Lys Gln Val Leu His Ser Trp Phe Arg Gln Pro Gln Ser Asn Trp Gly
                245                 250                 255
Ile Glu Ile Asn Ala Phe Asp Pro Ser Gly Thr Asp Leu Ala Val Thr
            260                 265                 270
Ser Leu Gly Pro Gly Ala Glu Gly Leu His Pro Phe Met Glu Leu Arg
    275                 280                 285
Val Leu Glu Asn Thr Lys Arg Ser Arg Arg Asn Leu Gly Leu Asp Cys
    290                 295                 300
Asp Glu His Ser Ser Glu Ser Arg Cys Cys Arg Tyr Pro Leu Thr Val
305                 310                 315                 320
Asp Phe Glu Ala Phe Gly Trp Asp Trp Ile Ile Ala Pro Lys Arg Tyr
                325                 330                 335
Lys Ala Asn Tyr Cys Ser Gly Gln Cys Glu Tyr Met Phe Met Gln Lys
            340                 345                 350
Tyr Pro His Thr His Leu Val Gln Gln Ala Asn Pro Arg Gly Ser Ala
        355                 360                 365
Gly Pro Cys Cys Thr Pro Thr Lys Met Ser Pro Ile Asn Met Leu Tyr
    370                 375                 380
Phe Asn Asp Lys Gln Gln Ile Ile Tyr Gly Lys Ile Pro Gly Met Val
385                 390                 395                 400
Val Asp Arg Cys Gly Cys Ser
            405
```

*FIG. 5*

SEQ ID NO: 2

```
Ala Glu Gly Pro Ala Ala Ala Ala Ala Ala Ala Ala Ala Ala Ala
1               5                   10                  15
Ala Gly Val Gly Gly Glu Arg Ser Ser Arg Pro Ala Pro Ser Val Ala
            20                  25                  30
Pro Glu Pro Asp Gly Cys Pro Val Cys Val Trp Arg Gln His Ser Arg
            35                  40                  45
Glu Leu Arg Leu Glu Ser Ile Lys Ser Gln Ile Leu Ser Lys Leu Arg
50                  55                  60
Leu Lys Glu Ala Pro Asn Ile Ser Arg Glu Val Val Lys Gln Leu Leu
65                  70                  75                  80
Pro Lys Ala Pro Pro Leu Gln Gln Ile Leu Asp Leu His Asp Phe Gln
                85                  90                  95
Gly Asp Ala Leu Gln Pro Glu Asp Phe Leu Glu Glu Asp Glu Tyr His
                100                 105                 110
Ala Thr Thr Glu Thr Val Ile Ser Met Ala Gln Glu Thr Asp Pro Ala
            115                 120                 125
Val Gln Thr Asp Gly Ser Pro Leu Cys Cys His Phe His Phe Ser Pro
    130                 135                 140
Lys Val Met Phe Thr Lys Val Leu Lys Ala Gln Leu Trp Val Tyr Leu
145                 150                 155                 160
Arg Pro Val Pro Arg Pro Ala Thr Val Tyr Leu Gln Ile Leu Arg Leu
                165                 170                 175
Lys Pro Leu Thr Gly Glu Gly Thr Ala Gly Gly Gly Gly Gly Gly Arg
            180                 185                 190
Arg His Ile Arg Ile Arg Ser Leu Lys Ile Glu Leu His Ser Arg Ser
            195                 200                 205
Gly His Trp Gln Ser Ile Asp Phe Lys Gln Val Leu His Ser Trp Phe
    210                 215                 220
Arg Gln Pro Gln Ser Asn Trp Gly Ile Glu Ile Asn Ala Phe Asp Pro
225                 230                 235                 240
Ser Gly Thr Asp Leu Ala Val Thr Ser Leu Gly Pro Gly Ala Glu Gly
                245                 250                 255
Leu His Pro Phe Met Glu Leu Arg Val Leu Glu Asn Thr Lys Arg Ser
            260                 265                 270
Arg Arg Asn Leu Gly Leu Asp Cys Asp Glu His Ser Ser Glu Ser Arg
        275                 280                 285
Cys Cys Arg Tyr Pro Leu Thr Val Asp Phe Glu Ala Phe Gly Trp Asp
    290                 295                 300
Trp Ile Ile Ala Pro Lys Arg Tyr Lys Ala Asn Tyr Cys Ser Gly Gln
305                 310                 315                 320
Cys Glu Tyr Met Phe Met Gln Lys Tyr Pro His Thr His Leu Val Gln
                325                 330                 335
Gln Ala Asn Pro Arg Gly Ser Ala Gly Pro Cys Cys Thr Pro Thr Lys
            340                 345                 350
Met Ser Pro Ile Asn Met Leu Tyr Phe Asn Asp Lys Gln Gln Ile Ile
        355                 360                 365
Tyr Gly Lys Ile Pro Gly Met Val Val Asp Arg Cys Gly Cys Ser
    370                 375                 380
```

*FIG. 6*

SEQ ID NO: 3

```
Asn Leu Gly Leu Asp Cys Asp Glu His Ser Ser Glu Ser Arg Cys Cys
1               5                   10                  15
Arg Tyr Pro Leu Thr Val Asp Phe Glu Ala Phe Gly Trp Asp Trp Ile
                20                  25                  30
Ile Ala Pro Lys Arg Tyr Lys Ala Asn Tyr Cys Ser Gly Gln Cys Glu
                35                  40                  45
Tyr Met Phe Met Gln Lys Tyr Pro His Thr His Leu Val Gln Gln Ala
        50                  55                  60
Asn Pro Arg Gly Ser Ala Gly Pro Cys Cys Thr Pro Thr Lys Met Ser
65                  70                  75                  80
Pro Ile Asn Met Leu Tyr Phe Asn Asp Lys Gln Gln Ile Ile Tyr Gly
                85                  90                      95
Lys Ile Pro Gly Met Val Val Asp Arg Cys Gly Cys Ser
                100                 105
```

FIG. 7

SEQ ID NO: 4

Ala Glu Gly Pro Ala Ala Ala Ala Ala Ala Ala Ala Ala Ala Ala
1               5                   10                  15
Ala Gly Val Gly Gly Glu Arg Ser Ser Arg Pro Ala Pro Ser Val Ala
            20                  25                  30
Pro Glu Pro Asp Gly Cys Pro Val Cys Val Trp Arg Gln His Ser Arg
            35                  40                  45
Glu Leu Arg Leu Glu Ser Ile Lys Ser Gln Ile Leu Ser Lys Leu Arg
        50                  55                  60
Leu Lys Glu Ala Pro Asn Ile Ser Arg Glu Val Val Lys Gln Leu Leu
65                  70                  75                  80
Pro Lys Ala Pro Pro Leu Gln Gln Ile Leu Asp Leu His Asp Phe Gln
                85                  90                  95
Gly Asp Ala Leu Gln Pro Glu Asp Phe Leu Glu Glu Asp Glu Tyr His
                100                 105                 110
Ala Thr Thr Glu Thr Val Ile Ser Met Ala Gln Glu Thr Asp Pro Ala
            115                 120                 125
Val Gln Thr Asp Gly Ser Pro Leu Cys Cys His Phe His Phe Ser Pro
    130                 135                 140
Lys Val Met Phe Thr Lys Val Leu Lys Ala Gln Leu Trp Val Tyr Leu
145                 150                 155                 160
Arg Pro Val Pro Arg Pro Ala Thr Val Tyr Leu Gln Ile Leu Arg Leu
                165                 170                 175
Lys Pro Leu Thr Gly Glu Gly Thr Ala Gly Gly Gly Gly Gly Gly Arg
            180                 185                 190
Arg His Ile Arg Ile Arg Ser Leu Lys Ile Glu Leu His Ser Arg Ser
            195                 200                 205
Gly His Trp Gln Ser Ile Asp Phe Lys Gln Val Leu His Ser Trp Phe
    210                 215                 220
Arg Gln Pro Gln Ser Asn Trp Gly Ile Glu Ile Asn Ala Phe Asp Pro
225                 230                 235                 240
Ser Gly Thr Asp Leu Ala Val Thr Ser Leu Gly Pro Gly Ala Glu Gly
                245                 250                 255
Leu His Pro Phe Met Glu Leu Arg Val Leu Glu Asn Thr Lys Arg Ser
            260                 265                 270
Arg Arg

*FIG. 8*

TREATMENT WITH GDF11 PREVENTS WEIGHT GAIN, IMPROVES GLUCOSE TOLERANCE AND REDUCES HEPATOSTEATOSIS

RELATED APPLICATIONS

This application is a national stage filing under 35 U.S.C. 371 of International Application No. PCT/US2017/012505, filed Jan. 6, 2017, which claims the benefit of U.S. Provisional Application No. 62/275,645, filed Jan. 6, 2016. The entire teachings of the above applications are incorporated herein by reference. International Application No. PCT/US2017/012505 was published under PCT Article 21(2) in English.

BACKGROUND OF THE INVENTION

Impaired glucose tolerance and increased hepatosteatosis are associated with obesity and increasing age in both mice and humans. These defects are attributed to increasing adiposity and insulin resistance. Age-associated decline in beta cell function also plays an important role by contributing to relative insulin insufficiency. Impaired glucose tolerance and impaired fasting glucose form an intermediate stage in the progression of diabetes mellitus (e.g., Type 1, Type 2 and gestational diabetes) and contribute to declines in metabolic health.

Needed are compositions and methods to reduce the risk of developing one or more metabolic diseases, such as diabetes. Also needed are compositions and methods of preventing or treating obesity and the associated impairments in metabolic health relating to obesity. Also needed are compositions and methods for preventing or treating hepatosteatosis in a subject.

SUMMARY OF THE INVENTION

The compositions and methods disclosed herein relate to the findings that growth differentiation factor 11 (GDF11) may be used to prevent, and in certain embodiments treat certain age- and/or obesity-associated metabolic diseases, such as impairments in glucose tolerance, insulin resistance and hepatosteatosis. For example, the methods and compositions disclosed herein for preventing or reducing obesity in a subject cause a corresponding reduction in the development of metabolic diseases or co-morbidities associated with obesity. Also disclosed herein are novel compositions and methods for preventing, and in certain instances treating, obesity and the associated impairments in metabolic health. In certain aspects, the compositions and methods disclosed herein can be used to prevent weight gain or obesity, improve glucose tolerance and/or prevent hepatosteatosis in a subject.

The work described herein generally relates to the findings that the administration of GDF11 prevents weight gain in animals administered a high fat diet. In certain embodiments, disclosed herein are methods of reducing and/or treating hepatosteatosis in a subject in need thereof, such methods comprising a step of administering to the subject a composition which increases GDF11 polypeptide in the subject and thereby reduces or treats hepatosteatosis in the subject.

Also disclosed are methods of preventing, inhibiting and/or treating one or more metabolic diseases (e.g., diabetes) in a subject in need thereof, such methods comprising a step of administering to the subject a composition which increases GDF11 polypeptide in the subject. Such administration of the composition (e.g., a composition comprising human GDF11 polypeptide or a functional fragment or variant thereof) to the subject reduces weight gain and/or obesity in the subject and thereby prevents, inhibits and/or treats the one or more metabolic diseases in the subject. For example, in certain aspects the compositions and methods disclosed herein may be administered to a subject (e.g., a subject with a family history of metabolic disease) to slow or prevent the development of weight gain and/or obesity in such subject, thereby reducing or mitigating the risk that such subject will develop the metabolic disease.

In certain aspects, also disclosed herein are methods of treating or preventing glucose intolerance in a subject in need thereof, such methods comprising a step of administering to the subject a composition which increases GDF11 polypeptide in the subject and thereby treating or preventing glucose intolerance in the subject.

In some embodiments, the present inventions relate to methods of treating and/or preventing a metabolic disease (e.g., Type II diabetes) in a subject in need thereof, such methods comprising a step of administering to the subject a composition which increases GDF11 polypeptide in the subject, and thereby treating and/or preventing the metabolic disease.

In certain aspects, the methods disclosed herein comprise a step of administering to a subject a composition which increases GDF11 protein or polypeptide in the subject (e.g., administering a human GDF11 polypeptide or a functional fragment or variant thereof). For example, in some embodiments, such a composition comprises a GDF11 polypeptide (e.g., human recombinant GDF11) or a functional fragment or variant thereof (e.g., a non-naturally occurring functional variant of human GDF11). In some embodiments, the GDF11 polypeptide or a functional fragment or variant thereof is recombinantly prepared. In certain aspects, the composition stimulates the endogenous expression and/or production of GDF11 in the subject. In any of the foregoing embodiments, the compositions may be administered to a subject by any suitable routes of administration. For example, in certain aspects the compositions disclosed herein (e.g., a composition comprising recombinantly-prepared human GDF11 protein) are administered to a subject via a route of administration selected from the group consisting of enterally, intravenously, subcutaneously, intramuscularly and intrathecally. In certain aspects, an effective amount of the composition is administered to the subject. For example, in certain aspects, the GDF11 polypeptide is administered to the subject at a dose (e.g., a daily dose) of about 0.1 mg/kg/day, about 0.25 mg/kg/day, about 0.3 mg/kg/day, about 0.5 mg/kg/day, about 0.75 mg/kg/day, about 1.0 mg/kg/day, about 1.25 mg/kg/day, about 1.5 mg/kg/day, about 2.0 mg/kg/day, or more.

In some embodiments, the compositions disclosed herein comprise a human GDF11 polypeptide or a functional fragment or variant thereof (e.g., a non-naturally occurring, functional GDF11 variant). In certain aspects of any of the foregoing embodiments, the GDF11 polypeptide is recombinantly prepared. In certain aspects of any of the foregoing embodiments, the compositions disclosed herein further comprise a pharmaceutically-acceptable carrier. In certain embodiments, the compositions disclosed herein may be formulated for daily, weekly, bi-weekly, monthly, bi-monthly, quarterly, biannual, semi-annual or annual administration. For example, in certain embodiments, the GDF11 polypeptide may be modified (e.g., PEGylated, mutated or coupled to Fc) to impart one or more desired characteristics to the polypeptide (e.g., to extend its therapeutic activity).

In some embodiments, the methods disclosed herein cause an increase in the concentration of GDF11 protein or polypeptide in the subject (e.g., as measured in the serum or tissues of the subject). For example in certain aspects, the concentration of GDF11 protein or polypeptide is increased by at least about 5%, about 10%, about 20%, about 30%, about 40%, about 50%, about 60%, about 70%, about 80%, about 90%, about 100% or more in the subject. In certain aspects, the concentration of GDF11 protein or polypeptide is increased to at least about 75%, at least about 80%, at least about 85%, at least about 90%, at least about 95%, at least about 97.5%, at least about 99% or more of a healthy GDF11 reference level in the subject.

The compositions and methods disclosed herein are useful for the prevention or treatment of one or more metabolic diseases. For example, such compositions and methods may be used to treat one or more metabolic diseases selected from the group consisting of Type I diabetes, Type II diabetes, gestational diabetes, insulin resistance, metabolic syndrome, obesity, impaired glucose tolerance, impaired fasting glucose, and hepatosteatosis. In certain aspects of any of the foregoing embodiments, the metabolic disease is diabetes. In certain aspects of any of the foregoing embodiments, the metabolic disease is hepatosteatosis.

In some aspects of any of the foregoing embodiments, the subject is a mammal. In some aspects of any of the foregoing embodiments, the subject is a human. In certain embodiments, the subject is an adult (e.g., an aged adult).

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A compares the results of baseline glucose tolerance testing (GTT) performed at Day 0 in those aged mice randomized to receive phosphate buffered saline (saline) and those aged mice randomized to receive GDF11. FIG. 2B illustrates the results of GTT performed at Day 7 in those aged mice randomized to receive phosphate buffered saline (saline) and those aged mice randomized to receive GDF11. FIG. 2C depicts the results of GTT performed at Day 28 in those aged mice randomized to receive phosphate buffered saline (saline) and those aged mice randomized to receive GDF11.

FIG. 3A depicts the results of H&E staining of liver tissues of both the saline and GDF11 treated aged mice and demonstrates that such GDF11 treated mice had reduced hepatosteatosis compared to PBS treated animals fed a high fat diet. FIG. 3B illustrates that GDF11 reduced hepatosteatosis in the GDF11 treated mice compared to the saline treated mice.

FIG. 5 shows the amino acid sequence encoding a human GDF11 precursor polypeptide (SEQ ID NO: 1).

FIG. 6 shows the amino acid sequence encoding a human GDF11 pro-peptide (SEQ ID NO: 2).

FIG. 7 shows the amino acid sequence encoding a human mature GDF11 polypeptide (SEQ ID NO: 3).

FIG. 8 shows the amino acid sequence encoding a human GDF11 N-terminal polypeptide (SEQ ID NO: 4).

DETAILED DESCRIPTION OF THE INVENTION

Figure 1:
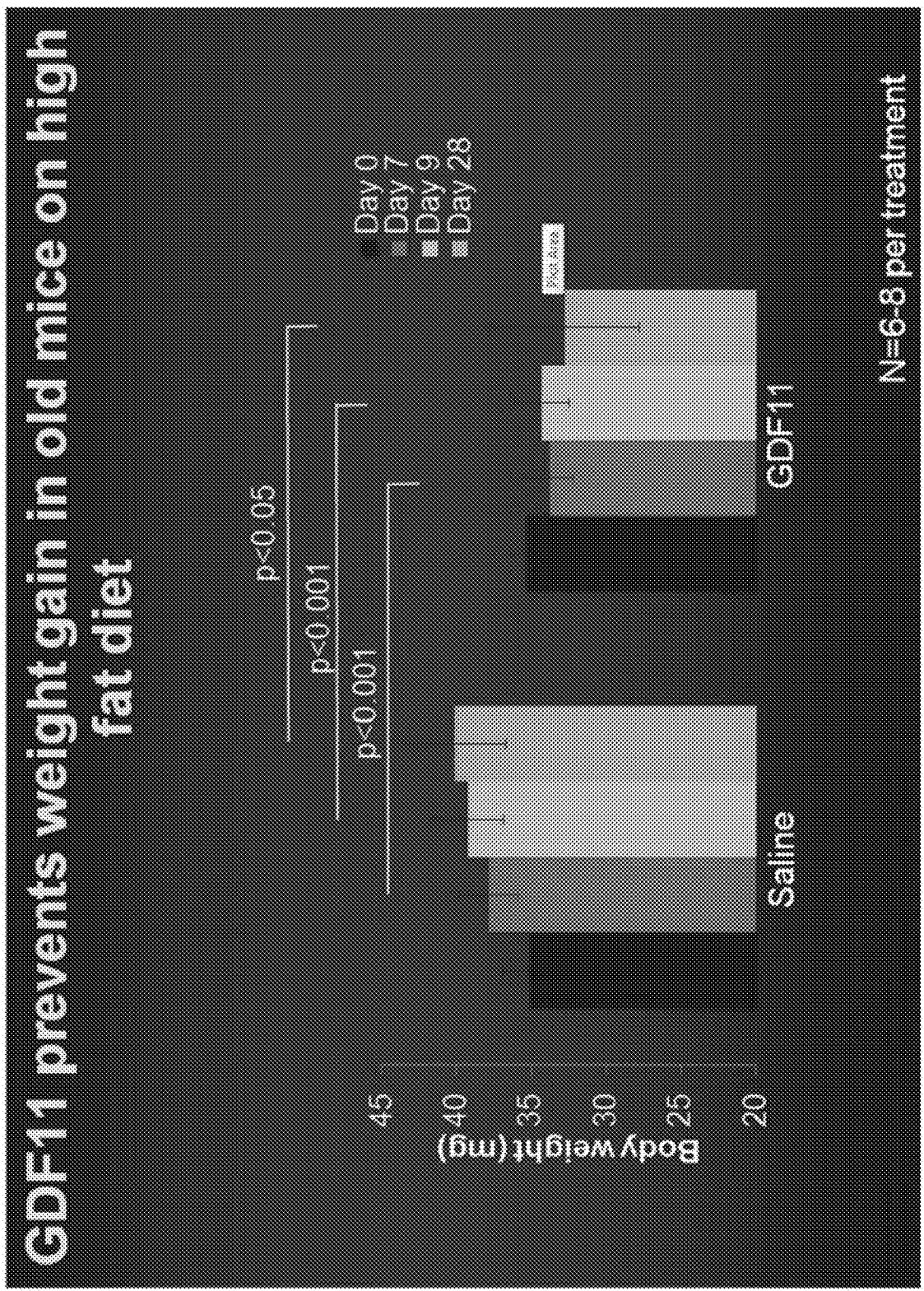
FIG. 1 illustrates the results of studies described herein and confirms that GDF11 prevents weight gain in old mice administered a high fat diet.

Obesity and increasing age are both known to contribute to the development of metabolic diseases, which include, for example, diabetes, impaired glucose tolerance and impaired fasting glucose. The development or progression of such metabolic diseases (e.g., diabetes mellitus) contributes to the overall decline in the subject's health. Disclosed herein are compositions and methods that relate to the findings that GDF11 prevents weight gain, improves glucose tolerance and reduces hepatosteatosis in aged mice that were administered a high fat diet. In particular, the methods and compositions described herein relate to increasing the level of GDF11 polypeptide in a subject, thereby treating or preventing the development of obesity in the subject, reducing the metabolic consequences of obesity and improving the subject's metabolic health.

As used herein, the term "GDF11" refers to "Growth and Differentiation Factor 11" (NCBI Gene ID No: 10220), which is a member of the Transforming Growth Factor-beta superfamily of growth factors. GDF11 is known to bind TGFβ3 superfamily type I receptors including ALK4, ALK5, and ALK7. For signaling in mammalian development, GDF11 predominantly uses ALK4 and ALK5. In some embodiments, GDF11 signaling can also occur via the ACVR2B receptor. As used herein, "GDF11" can include the human precursor polypeptide (SEQ ID NO: 1, depicted in FIG. 5; NCBI Ref Seq: NP _005802); the human pro-peptide (SEQ ID NO: 2, depicted in FIG. 6); the human N-terminal polypeptide (SEQ ID NO: 4, depicted in FIG. 8), and the human mature (SEQ ID NO: 3, depicted in FIG. 7) forms of GDF11 as well as homologs from other species, including but not limited to bovine, dog, cat, chicken, murine, rat, porcine, bovine, turkey, horse, fish, baboon and other primates. The terms also refer to fragments or variants of GDF11 (e.g., non-naturally occurring variants) that maintain at least 50% of the effects (e.g., the effects of preventing weight gain or preventing, inhibiting or treating or otherwise reducing the incidence of metabolic disease) of the full length GDF11 of SEQ ID NO: 1, SEQ ID NO: 2, or SEQ ID NO: 3, for example, as measured in an appropriate animal model (e.g., aged mice administered a high fat diet).

In certain aspects, the GDF11 proteins or polypeptides disclosed herein have been modified (e.g., modified to extend the therapeutic activity of such GDF11 protein or polypeptide). In certain aspects, the GDF11 proteins or polypeptides have been modified such that they are non-naturally occurring variants of GDF11 (e.g., functional variants of human GDF11). Conservative substitution variants that maintain the effects of wild type GDF11 will include a conservative substitution as defined herein. The identification of amino acids most likely to be tolerant of conservative substitution while maintaining at least 50% of the activity of the wild type GDF11 is guided by, for example, sequence alignment with GDF11 homologs or paralogs from other species. Amino acids that are identical between GDF11 homologs are less likely to tolerate change, while those showing conservative differences are much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model (e.g., aged mice that are administered a high fat diet).

For human GDF11, the pro-peptide plus signal sequence (e.g. the precursor polypeptide) is 407 amino acids long. Cleavage of the 24 amino acid signal peptide generates a pro-peptide of 383 amino acids and cleavage of the pro-peptide results in a mature GDF11 polypeptide of 109 amino acids that corresponds to the C-terminal 109 amino acids of the pro-peptide. The mature polypeptide forms a disulfide-linked homodimer. Cleavage of the pro-peptide also generates the N-terminal polypeptide (e.g., SEQ ID NO: 4) comprising amino acids 25-298 of SEQ ID NO: 1. The N-terminal GDF11 polypeptide can antagonize the activity of, e.g., the polypeptides of SEQ ID NOs: 2 and 3, at least in vitro by forming a complex with other forms of GDF11 polypeptides and can thus be used to modulate the activity of GDF11 compositions as described herein. Thus, to the extent that GDF11 polypeptides as described herein prevent the development of obesity, and to the extent the N-terminal GDF11 polypeptide of, e.g., SEQ ID NO: 4, can antagonize such effects, the polypeptide of SEQ ID NO: 4 can be excluded from the meaning of "GDF11 polypeptide" as that term is used herein.

As used herein, the terms "proteins" and "polypeptides" are used interchangeably to designate a series of amino acid residues connected to the other by peptide bonds between the alpha-amino and carboxy groups of adjacent residues. The terms "protein," and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when refining to a gene product and fragments thereof. Thus, exemplary polypeptides or proteins include gene products, naturally occurring proteins, homologs, orthologs, paralogs, fragments and other equivalents, as well as both naturally and non-naturally occurring variants, fragments, and analogs of the foregoing.

In certain aspects, GDF11 may be modified (e.g., modified to extend its therapeutic activity). As used herein, the term "modified" generally refers to changing GDF11 to impart one or more properties or to alter the activity of GDF11 in a selective manner, so as to cause GDF11 to exert a desired physiological effect. It should be noted that in certain embodiments, modification includes coupling GDF11 to one or more secondary compounds or molecules (e.g., coupling GDF11 or a fragment or variant thereof to a fusion protein or to one or more polymers). In certain embodiments, GDF11 may be modified to include a mutation. In certain embodiments, GDF11 may be modified by coupling to Fc. In still other embodiments, GDF11 may be modified by coupling to one or more polymers (e,g., PEG). In certain embodiments, the modification may comprise one or more chemical modifications to GDF11, for example, by altering the amino acids encoding the GDF11 protein.

In certain aspects, GDF11 is modified to introduce one or more exogenous nucleic acids into the sequence encoding GDF11. Accordingly, it should be appreciated that the term modified is intended to include the introduction of one or more modified nucleic acids into the sequences encoding GDF11 and may include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages.

As used herein, the term "pro-peptide" as used with reference to GDF11 refers to a GDF11 polypeptide in which the signal domain (e.g. amino acids 1-24 of SEQ ID NO: 1) has been cleaved off during formation of the mature and/or active forms of GDF11. As used herein, the term "precursor peptide" is used with reference to a GDF11 polypeptide comprising the signal domain (e.g., a polypeptide comprising the amino acid sequence of SEQ ID NO: 1).

The compositions and methods disclosed herein are useful for the prevention, or in certain instances the treatment, of obesity, weight gain, hepatosteatosis and/or one or more metabolic diseases. As used herein, the term "metabolic disease" generally refers to disorders affecting a subject in which errors of metabolism, imbalances in metabolism, or suboptimal metabolism occur and include, for example, impaired glucose tolerance, insulin resistance, diabetes mellitus and/or hepatosteatosis. In certain embodiments, the metabolic disease relates to or develops as a result of a condition. For example, obesity may contribute to the development or progression of diabetes, rendering an obese subject at an increased risk for the development of the metabolic disease.

In certain aspects, the compositions and methods disclosed herein may be used to treat one or more metabolic diseases selected from the group consisting of Type I diabetes, Type II diabetes, gestational diabetes, insulin resistance, metabolic syndrome, obesity, impaired glucose tolerance, impaired fasting glucose, and hepatosteatosis. In certain aspects, the metabolic disease is diabetes. In certain aspects, the metabolic disease is hepatosteatosis.

In some embodiments, the compositions and methods disclosed herein are useful for reducing or otherwise mitigating the risk that a subject will develop a metabolic disease, or in certain instances are useful for slowing or preventing the metabolic consequences associated with obesity. For example, such compositions and methods may be administered to a subject that is at risk for developing a metabolic disease (e.g., a subject with a family history of diabetes) and thereby reduce or mitigate the risk that such subject will develop the metabolic disease. Similarly, in certain aspects such compositions and methods may be administered to a subject (e.g., a subject with a family history of metabolic disease) to slow or prevent the development of obesity in such subject and thereby reduce or mitigate the risk that such subject will develop the metabolic disease. In some embodiments, the subject's risk of developing the metabolic disease is reduced or reversed by about at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 33%, at least 35%, at least 41%, at least 44%, at least 50%, at least 60%, at least 70%, at least 75%, at least 80%, at least 90%, at least 95%, at least 97%, at least 99%, or at least 100%.

It should be understood that the present inventions are not limited to reducing, preventing, inhibiting or mitigating the risk of one or more metabolic diseases. Rather, also contemplated are methods of treating one or more metabolic diseases using the compositions and methods that are disclosed herein. For example, an effective amount of the compositions disclosed herein may be administered to an obese subject to treat the subject's obesity (e.g., to cause a reduction in the subject's weight), and thereby reduce the risk that the subject will experience further deterioration in their metabolic disease. In certain embodiments, the methods and compositions disclosed herein are coupled with one or more non-pharmacological interventions. For example, the compositions disclosed herein may be administered in combination with one or more lifestyle modifications (e.g., diet, exercise and/or smoking cessation therapy).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. A subject may include any subset of the foregoing, e.g., all of the above, but excluding one or more groups or species such as humans, primates or rodents. In certain embodiments, the subject is a mammal, e.g., a primate, e.g., a human. Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, obesity and/or metabolic disease. In addition, the methods described herein can be used to treat domesticated animals and/or pets. A subject can be male or female. A subject can be one who has been previously diagnosed with or identified as suffering from or having a condition, disease, or disorder described herein in need of treatment of one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition.

A "subject in need" of treatment for a particular condition can be a subject having that condition, diagnosed as having that condition, or at increased risk of developing that condition relative to a given reference population. For example, in certain embodiments, a subject in need may have a family history or predisposition to developing one or more metabolic diseases (e.g., diabetes) and would thus be considered a candidate for receiving treatment in accordance with methods and compositions disclosed herein. Similarly, in certain embodiments a subject in need may be obese and thus predisposed to developing one or more metabolic diseases and would thus also be considered a candidate for receiving treatment in accordance with the methods and compositions disclosed herein.

In certain aspects, the methods disclosed herein comprise administering to a subject a composition which increases the level or concentration of GDF11 polypeptide in the subject. In some embodiments, the subject is one who has, or has been diagnosed as having or as being at an increased risk of developing a metabolic disease or condition. In certain aspects, the subject is at an increased risk of developing the metabolic disease or condition due to aging, advanced age, obesity and/or other co-morbidities. As is used herein, a condition, disease, or disorder "due to aging" refers to one such condition, disease, or disorder which is at least partially attributable to a subject's age. In some embodiments, the subject is an adult subject. In some embodiments, the subject is an elderly subject. In some embodiments, an elderly subject is over the age of 50, 55, 60, 65, 70, 75, 80, 85, 90, or 100 years.

In some embodiments, the level of GDF11 polypeptide is determined by measuring the level of GDF11 in the circulation of a subject. In some embodiments, the level of GDF11 polypeptide is the level of GDF11 measured or detected in the serum or tissue of a subject. In some embodiments, the level of GDF11 polypeptide is determined by measuring the level of an mRNA encoding a GDF11 polypeptide. The level of GDF11 in a subject can be determined by obtaining a biological sample from the subject and determining the level of GDF11 in the biological sample. Methods for determining the level of a polypeptide in a subject or a sample obtained from a subject are well known in the art and include, but are not limited to, ELISA, radioimmunoassay, immunohistochemistry, methods involving a labeled antibody specific for GDF11, dot blot analysis, functional bioassays, Northern blot, in-situ hybridization, and RT-PCR, aptamer-based proteomic technology (e.g., SOMAscan™ commercially available from SomaLogic, Inc.) among others. Antibodies specific for GDF11 are commercially available, e.g. Cat. No. ab71347 from Abeam: Cambridge, Mass. In some embodiments, the antibodies are selective GDF11 monoclonal antibodies. In some embodiments, the level of GDF11 can be measured as described in Souza et al., Molecular Endocrinology 2008 22:2689-2702; which is incorporated by reference herein in its entirety.

In some embodiments, the compositions disclosed herein comprise a human GDF11 polypeptide or a functional fragment or variant thereof. In certain aspects, the compositions disclosed herein further comprise a pharmaceutically-acceptable carrier. The methods and compositions of the present invention and selection of pharmaceutically acceptable carriers and excipients are described in detail in, for example, L. William, Remington: The Science and Practice of Pharmacy. $22^{nd}$ ed. Pharmaceutical Press (2012), the entire contents of which are incorporated herein by reference. In certain aspects the compositions disclosed herein are formulated for administration on a daily, monthly, quarterly or annual basis. For example, the GDF11 compositions disclosed herein may be PEGylated or mutated or coupled to Fc to extend the activity of such compositions.

Aspects of the disclosure involve employing effect amounts of GDF11. An "effective amount" or "effective dose" of GDF11 (or a composition containing GDF11) generally refers to the amount sufficient to achieve a desired biological and/or pharmacological effect, e.g., when contacted with a cell in vitro or administered to a subject according to a selected administration form, route, and/or schedule. As will be appreciated by those of ordinary skill in the art, the absolute amount of GDF11 that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or through use of multiple doses, in various embodiments. It will be understood that the GDF11 compositions disclosed herein may be employed in an amount effective to achieve a desired biological and/or therapeutic effect. In some embodiments, an "effective amount" refers to an amount of an agent or composition described herein which, for example, reduces the risk that the subject will gain weight or suffer from one or more metabolic diseases. In some embodiments, an "effective amount" refers to an amount of GDF11 or composition described herein which prevents weight gain in response to the administration of a high fat diet. The skilled artisan can readily determine the effective amount of an agent or composition described herein for achieving its effective purpose using routine methods, without undue experimentation. It should be understood that in certain embodiments, an effective amount of the compositions disclosed herein may be administered to a subject for a limited period of time (e.g., several days, weeks or months). In certain embodiments, the agents and compositions disclosed herein may be administered to a subject in conjunction with, for example, lifestyle modifications (e.g., an exercise program).

It is to be understood that the inventions disclosed herein are not limited in their application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain compositions, methods and assays of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group of members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

Mice fed a high fat diet become obese, glucose intolerant and insulin resistant and the present investigators conducted the following studies to determine whether treatment with GDF11 prevents weight gain, improves glucose tolerance and reduces hepatosteatosis in aged mice fed a high fat diet.

Chow fed aged (23 months old) mice were weighed and subjected to intraperitoneal glucose tolerance tests (GTT) to assess their baseline weight and glucose tolerance. The mice were subsequently fed a high fat diet (HFD) and randomly treated with either PBS or GDF11 for 1 week and 1 month. Following treatment the animals were again weighed and subjected to GTTs. As illustrated in FIG. 1, treatment of aged animals fed a high fat diet with GDF11 prevented the weight gain observed in the PBS treated animals.

Figures 2A, 2B, 2C:
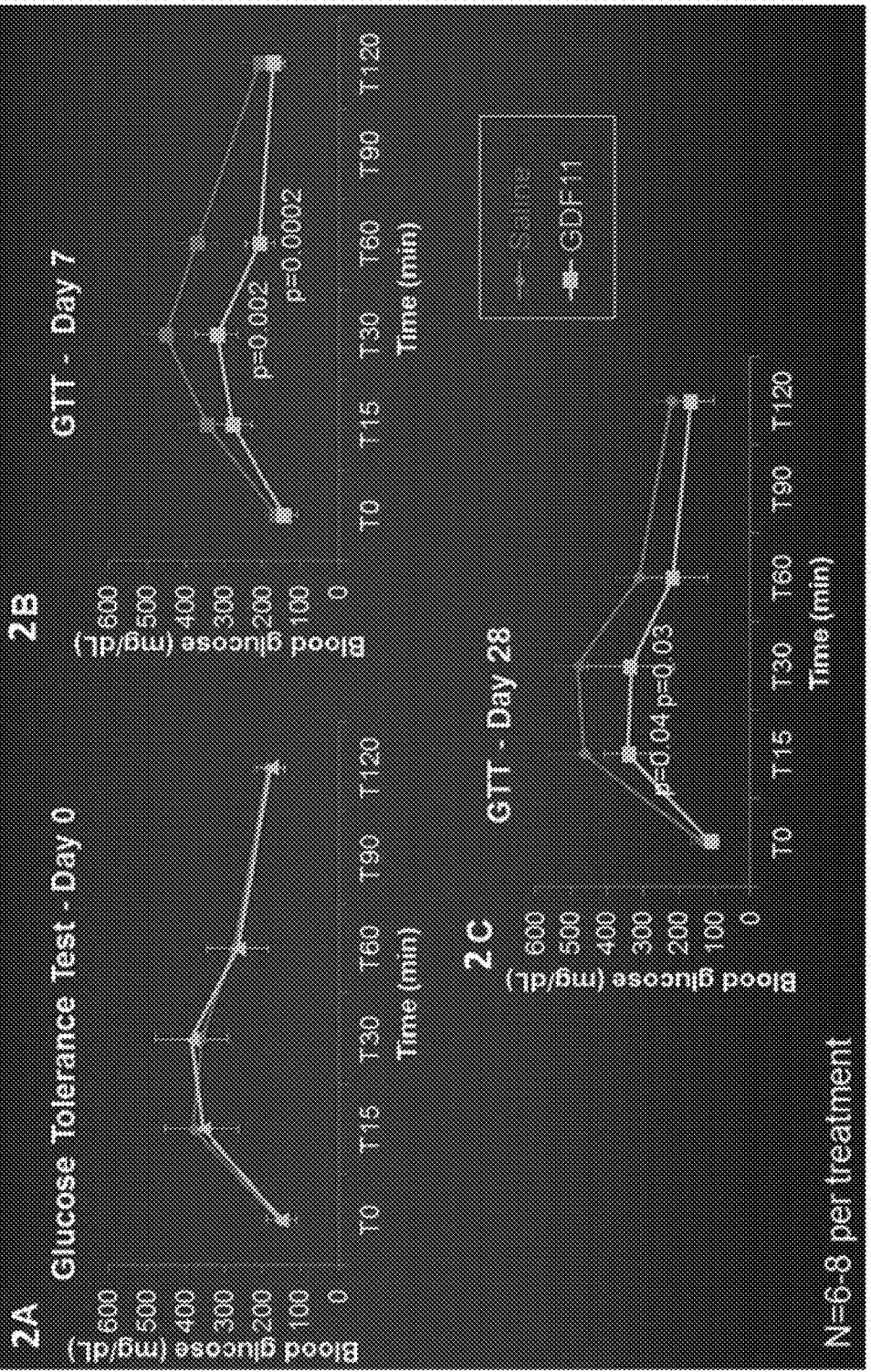
FIGS. 2A-2C demonstrate that GDF11 improves glucose tolerance in old mice fed a high fat diet at various time points.
Figures 3A, 3B:
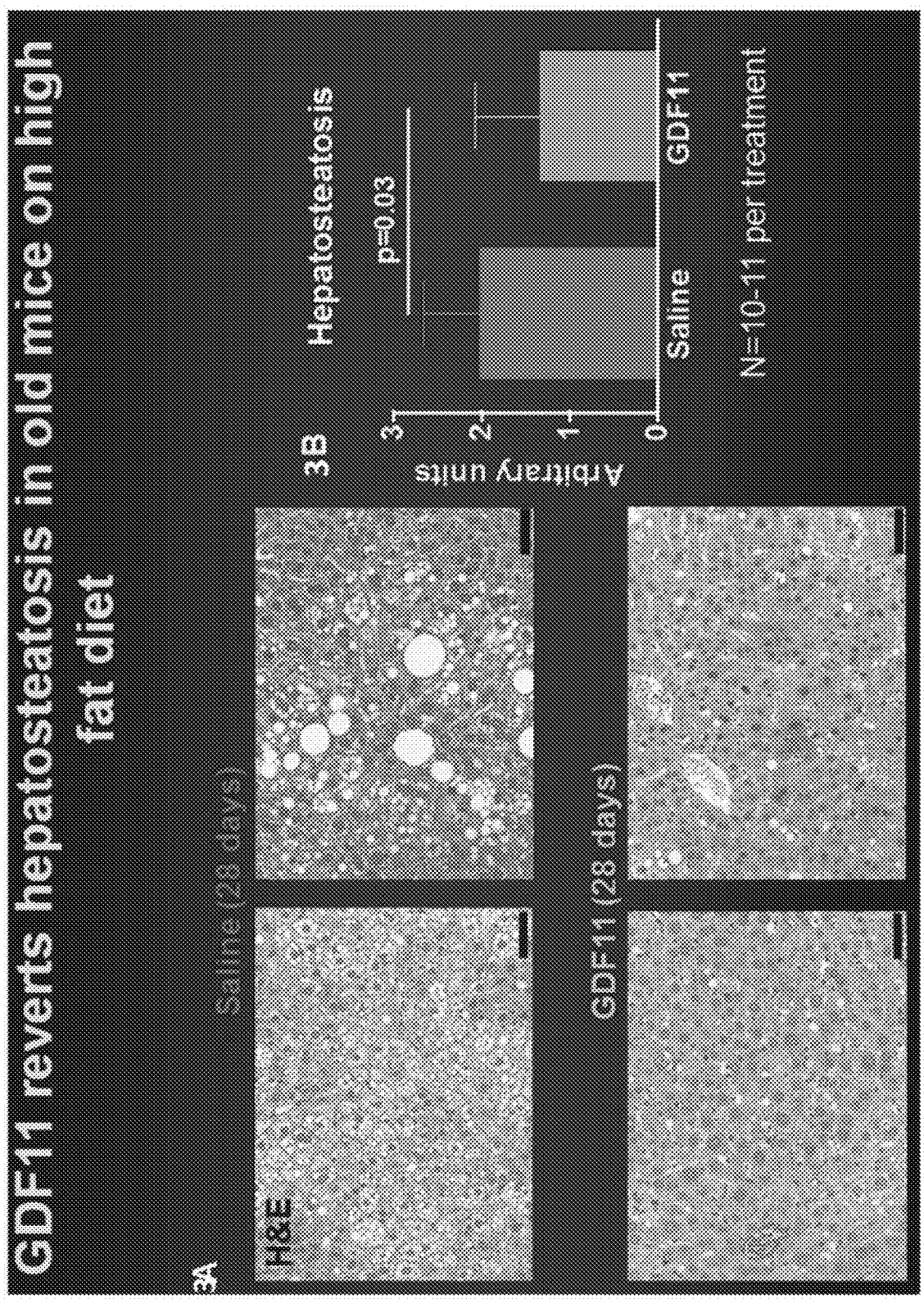
FIGS. 3A-3B show that GDF11 reverts hepatosteatosis in aged mice that were fed a high fat diet.

Compared to control mice fed a high fat diet treated with PBS, aged mice treated with GDF11 demonstrated significantly improved glucose tolerance, as depicted in FIGS. 2A-2C. After 1 month of treatment the animals were sacrificed and their livers harvested and processed for histological analysis. Microscopic histological analysis was performed to determine gross hepatosteatosis. As shown in FIGS. 3A-3B, aged animals treated with GDF11 were found to have significantly reduced hepatosteatosis compared to PBS treated animals fed a high fat diet.

Figure 4:
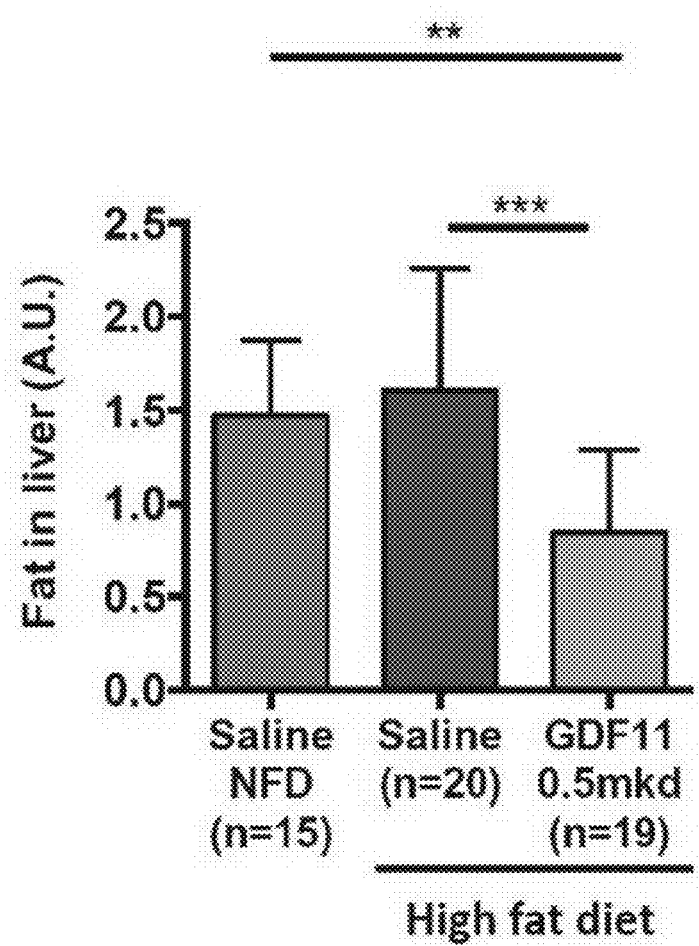
FIG. 4 shows that GDF11 treated animals on a high fat diet exhibited significantly reduced hepatosteatosis compared to control animals (normal fat diet or high fat diet), evidencing that GDF11 treatment can improve age-associated hepatosteatosis even in mice on a high fat diet.

In order to determine whether GDF11 treatment could improve a preexisting age-associated condition, the present inventors next performed histological analysis on livers dissected from control aged mice on a normal fat diet (NFD) and compared that to the histological analysis of livers from aged animals on a HFD treated with saline and GDF11. The present inventors found that aged mice on a NFD exhibited similar hepatosteatosis compared to aged mice on a HFD. As illustrated in FIG. 4, it was also determined that GDF11-treated animals on a HFD exhibited significantly reduced hepatosteatosis compared to control animals (NFD or HFD), evidencing that GDF11 treatment can improve age associated hepatosteatosis, even in mice on a HFD.

What is claimed is:

1. A method of inhibiting or treating hepatosteatosis in a subject in need thereof, comprising administering to the subject a composition which increases GDF11 polypeptide in the subject and thereby inhibiting or treating the hepatosteatosis in the subject, wherein the composition comprises an effective amount of GDF11 polypeptide or a functional fragment thereof.

2. The method of claim 1, wherein the GDF11 polypeptide is increased by at least about 100% in the subject.

3. The method of claim 1, wherein the GDF11 polypeptide is increased to at least 75% of a healthy reference level in the subject.

4. The method of claim 1, wherein the GDF11 polypeptide is a human GDF11 polypeptide.

5. The method of claim 1, wherein the GDF11 polypeptide is administered to the subject at a dose of about 0.5 mg/kg/day.

6. The method of claim 1, wherein the subject is a human.

7. The method of claim 6, wherein the subject is an adult.

8. The method of claim 1, wherein the composition further comprises a pharmaceutically-acceptable carrier.

9. The method of claim 8, wherein the composition is formulated for weekly administration to the subject.

10. The method of claim 8, wherein the composition is formulated for monthly administration to the subject.

11. The method of claim 8, wherein the composition is formulated for quarterly administration to the subject.

12. The method of claim 1, wherein the GDF11 polypeptide is modified.

13. The method of claims 12, wherein the modification is selected from the group consisting of a mutation, coupling to Fc and PEGylated GDF11.

\* \* \* \* \*

SEQUENCE LISTING

<160> NUMBER OF SEQ ID NOS: 4

<210> SEQ ID NO 1
<211> LENGTH: 407
<212> TYPE: PRT
<213> ORGANISM: Homo sapiens

<400> SEQUENCE: 1

Met Val Leu Ala Ala Pro Leu Leu Gly Phe Leu Leu Ala Leu
1               5                   10                  15

Glu Leu Arg Pro Arg Gly Glu Ala Ala Glu Gly Pro Ala Ala Ala
            20                  25                  30

Ala Ala Ala Ala Ala Ala Ala Gly Val Gly Gly Glu Arg Ser
            35                  40                  45

Ser Arg Pro Ala Pro Ser Val Ala Pro Glu Pro Asp Gly Cys Pro Val
        50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
            115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
            195                 200                 205

Ala Gly Gly Gly Gly Gly Arg Arg His Ile Arg Ile Arg Ser Leu
210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
            275                 280                 285

Val Leu Glu Asn Thr Lys Arg Ser Arg Arg Asn Leu Gly Leu Asp Cys
            290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
            355                 360                 365

```
Gly Pro Cys Cys Thr Pro Thr Lys Met Ser Pro Ile Asn Met Leu Tyr
        370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 2
<211> LENGTH: 383
<212> TYPE: PRT
<213> ORGANISM: Homo sapiens

<400> SEQUENCE: 2

Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
                20                  25                  30

Pro Glu Pro Asp Gly Cys Pro Val Cys Val Trp Arg Gln His Ser Arg
            35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
                85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125

Val Gln Thr Asp Gly Ser Pro Leu Cys Cys His Phe His Phe Ser Pro
    130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Gly Arg
            180                 185                 190

Arg His Ile Arg Ile Arg Ser Leu Lys Ile Glu Leu His Ser Arg Ser
        195                 200                 205

Gly His Trp Gln Ser Ile Asp Phe Lys Gln Val Leu His Ser Trp Phe
    210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
                245                 250                 255

Leu His Pro Phe Met Glu Leu Arg Val Leu Glu Asn Thr Lys Arg Ser
            260                 265                 270

Arg Arg Asn Leu Gly Leu Asp Cys Asp Glu His Ser Ser Glu Ser Arg
        275                 280                 285

Cys Cys Arg Tyr Pro Leu Thr Val Asp Phe Glu Ala Phe Gly Trp Asp
    290                 295                 300

Trp Ile Ile Ala Pro Lys Arg Tyr Lys Ala Asn Tyr Cys Ser Gly Gln
305                 310                 315                 320

Cys Glu Tyr Met Phe Met Gln Lys Tyr Pro His Thr His Leu Val Gln
                325                 330                 335
```

```
Gln Ala Asn Pro Arg Gly Ser Ala Gly Pro Cys Cys Thr Pro Thr Lys
                340                 345                 350

Met Ser Pro Ile Asn Met Leu Tyr Phe Asn Asp Lys Gln Gln Ile Ile
            355                 360                 365

Tyr Gly Lys Ile Pro Gly Met Val Val Asp Arg Cys Gly Cys Ser
        370                 375                 380

<210> SEQ ID NO 3
<211> LENGTH: 109
<212> TYPE: PRT
<213> ORGANISM: Homo sapiens

<400> SEQUENCE: 3

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 4
<211> LENGTH: 274
<212> TYPE: PRT
<213> ORGANISM: Homo sapiens

<400> SEQUENCE: 4

Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
        35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
                85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125

Val Gln Thr Asp Gly Ser Pro Leu Cys Cys His Phe His Phe Ser Pro
    130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175
```

-continued

```
Lys Pro Leu Thr Gly Glu Gly Thr Ala Gly Gly Gly Gly Gly Arg
            180             185             190

Arg His Ile Arg Ile Arg Ser Leu Lys Ile Glu Leu His Ser Arg Ser
        195             200             205

Gly His Trp Gln Ser Ile Asp Phe Lys Gln Val Leu His Ser Trp Phe
    210             215             220

Arg Gln Pro Gln Ser Asn Trp Gly Ile Glu Ile Asn Ala Phe Asp Pro
225             230             235             240

Ser Gly Thr Asp Leu Ala Val Thr Ser Leu Gly Pro Gly Ala Glu Gly
                245             250             255

Leu His Pro Phe Met Glu Leu Arg Val Leu Glu Asn Thr Lys Arg Ser
            260             265             270

Arg Arg
```